United States Patent [19]

Friedman et al.

[11] Patent Number: 4,829,005
[45] Date of Patent: May 9, 1989

[54] SEDIMENTATION FILTRATION MICROORGANISM GROWTH CULTURE SYSTEM

[76] Inventors: Michael P. Friedman, 920 Washington Ave., Haddonfield, N.J. 08033; James Jablonsky, 1610 Hedgewood Rd., Hatfield, Pa. 19440; Ronald F. Schell, 111 Fenwick Ct., Cherry Hill, N.J. 08034

[21] Appl. No.: 620,924

[22] Filed: Jun. 15, 1984

[51] Int. Cl.[4] .................. C12M 1/12; C12M 1/16; C12M 1/24; C12Q 1/24
[52] U.S. Cl. .................................... 435/296; 435/311; 435/299; 435/30; 210/416.1; 210/515; 210/321.84
[58] Field of Search ................ 435/30, 34, 292, 293, 435/294, 296, 299, 311, 810; 210/233, 235, 450, 416.1, 515, 321.84; 422/101

[56] References Cited

U.S. PATENT DOCUMENTS

| | | | |
|---|---|---|---|
| 2,879,207 | 3/1959 | Poitras | 435/292 |
| 3,295,686 | 1/1967 | Krueger | 435/311 X |
| 3,448,011 | 6/1969 | Russomanno | 435/296 X |
| 3,615,257 | 10/1971 | Frost et al. | 210/450 X |
| 3,616,253 | 10/1971 | D'Eustachio | 435/8 |
| 3,828,527 | 8/1974 | Briggs et al. | 210/450 X |
| 3,844,895 | 10/1974 | Rose et al. | 435/296 X |
| 3,929,583 | 12/1975 | Sharpe et al. | 435/311 X |
| 3,932,222 | 1/1976 | Dorn | 435/296 |
| 4,025,306 | 5/1977 | Studer | 435/292 X |
| 4,036,698 | 7/1977 | Bush et al. | 435/311 X |
| 4,038,150 | 7/1977 | Dorn et al. | 435/294 X |
| 4,410,630 | 10/1983 | Zierdt | 435/284 |
| 4,614,585 | 9/1986 | Mehra et al. | 210/450 X |

OTHER PUBLICATIONS

Davis et al., Microbiology, Second Edition, Harper & Row, Hagerstown, Md., 1973, pp. 454–455.

Primary Examiner—Robert J. Warden
Assistant Examiner—Randall E. Deck
Attorney, Agent, or Firm—Caesar, Rivise, Bernstein, Cohen & Pokotilow, Ltd.

[57] ABSTRACT

Apparatus for isolating and identifying microorganisms in blood or the like which comprises a tubular collection vessel which is sealed at both ends but includes means at one end for permitting the removal of fluid therein by the application of vacuum when the seal at that end is broken, a multisection filtration unit comprising a first section provided with means for receiving said one end of the collection vessel, means in said section for breaking the seal in said one end of the vessel when it is received by said first section, a second section of said filtration unit nested against the bottom of the first section, a filter membrane positioned between the nested first and second sections of said filtration unit, said filter membrane being in open communication with said one end of the collection vessel which is received by said first section, a third section of said filtration unit nested against the second section on the opposite side of the filter membrane from the nested first and second sections, and means for drawing a vacuum through the bottom of said third section whereby fluid in the collection vessel may be removed therefrom by said vacuum and passed through said filter membrane, organisms in said fluid being collected on said membrane.

2 Claims, 3 Drawing Sheets

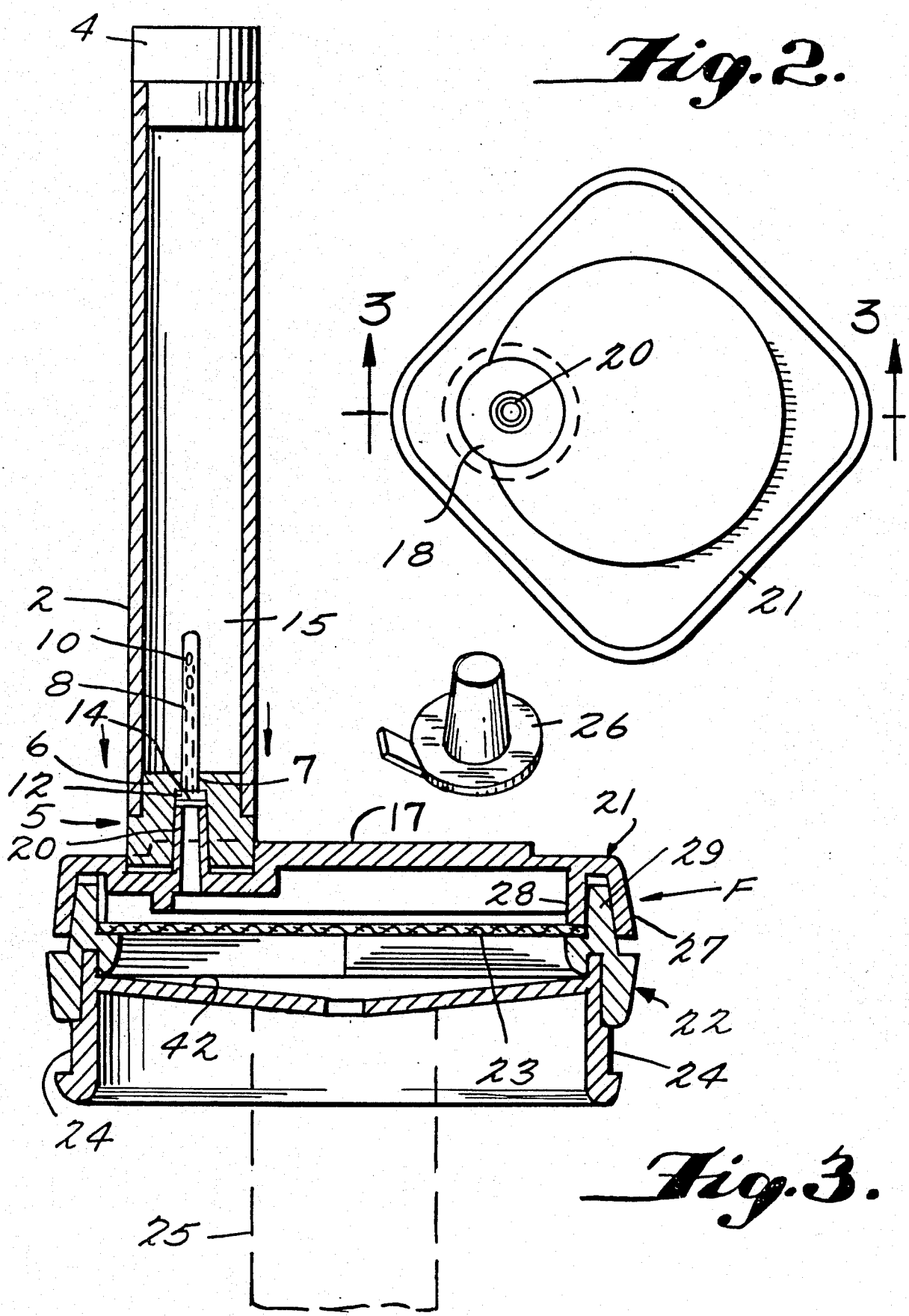

SEDIMENTATION FILTRATION MICROORGANISM GROWTH CULTURE SYSTEM

BACKGROUND AND SUMMARY OF THE INVENTION

The present invention is concerned with an improved apparatus and method for detecting, identifying and testing microorganisms isolated from liquids, particularly but not necessarily blood or other body fluids.

One particularly important area of use for the present invention is in the diagnosis of bacteremia. Bacteremia is a clinically significant, potentially life-threatening event. Despite the availability of a number of effective antimicrobial agents, the rate of mortality associated with bacteremia remains high. Recovery from bacteremia is increased when appropriate antimicrobial therapy is instituted early in the course of infection. Therefore, prompt detection, identification and susceptibility testing of microorganisms isolated from blood is imperative.

Procedures for diagnosing bacteremia require rapid isolation of the infecting organism. Culturing blood in a growth medium using commercially available blood culture bottles is the standard isolation technique. However, this technique has several disadvantages. Thus, for example, detection can be affected by the type of medium, the density of bacteria in blood, the time of collection, the volume of blood, the host's immune response, laboratory practices and other factors. In addition, several hours or days may be required to obtain results, depending on the bacteria's growth characteristics.

All of the above noted factors cause delays in obtaining the required diagnosis. Additionally, contamination is a real problem and the indicated test procedures can lead to inaccuracies in the diagnosis itself.

Much time and effort have been spent over many years in the search for more effective alternative methods to speed the isolation and identification of infecting bacteria. Various techniques for concentrating and isolating microorganisms from blood have been explored with little success. Sedimentation-filtration, lysis-filtration with measure of impedance and, more recently, charcoal hemoperfusion of the patient's blood have all been utilized. However, each method has suffered from one or more significant drawbacks. Typical problems include clogging of filters with serum and cells, toxicity of lysing solutions, contamination and decreased sensitivity. As a consequence, there has only been limited acceptance of previously available systems by clinical microbiology laboratories.

The present invention offer an improved method and apparatus for detecting and identifying microorganisms in blood or other body fluids or the like which avoid or substantially reduce the number of problems encountered with previously available approaches. A number of the advantages of the present method and apparatus are detailed hereinafter. Broadly speaking, however, the invention provides a relatively quick, simple and accurate bacterial culture system for isolating and identifying microorganisms, particularly those isolated from the blood or other body fluids.

The invention is based, to a significant extent, on a special combination and adaptation of centrifugation, filtration and growth media techniques which cooperate to expedite the recovery and identification of microorganisms from blood or the equivalent. Typically, according to the invention, fresh whole human blood is mixed with a fluid density gradient in a specially designed collection tube generally similar to the conventional vacutainer. The tube is centrifuged in standard manner for a suitable period of time, e.g. 30 minutes or so, to separate erythrocytes by sedimentation. The remaining fluid (plasma, leukocytes and fluid gradient) is then vacuum drawn from the tube through a special membrane filter after which a media cup containing a selected growth or culture medium is attached to the base of the filter to promote bacterial growth. The collected microorganisms are then detected on the filter within an appropriate culture period, e.g. 18–24 hours. The collection tube and filter unit are so designed that the tube may be sealed into the filter unit for application of the filtration vacuum before the tube contents are open to the vacuum whereby possible contamination of the fluid is kept to a minimum. The media cup likewise has a special sealing connection to the filter unit and the filter membrane is tightly sealed within the filter unit itself to avoid contamination. Additionally, the media cup is positioned close to, i.e. just below and functionally in contact with, the filter membrane so that the microorganisms collected on the filter membrane can be cultivated essentially "in situ".

The system of the invention is effective and sensitive for the recovery and detection of organisms in blood fluids or the like even when the organisms are present in very small amounts. Tests conducted with seeded or inoculated human blood, using concentrations of inocular in the range of from $3.0 \pm 0.7$ to $18.0 \pm 3.6$ organisms per ml have been successfully conducted and indicate no statistically significant differences detectable between the number of microorganisms recovered by the present system and by the conventional culture of the original inoculum.

The invention is useful in detecting any type of known micro-organism larger than viruses which may be found in the analysis of blood, other body fluid or the like. Typical of such microorganisms are *Candida albicans, Escherichia coli, Haemophilus influenzae, Klebsiella pneumoniae, Listeria monocytogenes, Neisseria meningitidis, Pseudomonas aeruginosa, Staphyllococcus aurias, Streptococcus faecalis,* and *Streptococcus pneumoniae.* These microorganisms have been detected on the filter membrane, using the method and apparatus of the invention, within 18 hours after filtration. Detection times will vary depending on various factors, for example, the amount of micro-organisms present. Thus, in tests using blood inoculated with the above listed micro-organisms, it has been found that detection time is decreased by 3 to 4 hours with each four to five-fold increase in inoculum. Similar results have been obtained with anaerobic organisms such as *Bacteroides fragilis, Fusobacterium nucleatum, Peptococcus asaccharolyticus, Peptostreptococcus micros* and *Veilonella parvula.*

It will be recognized by those in the art that the combination of centrifugation and filtration procedures contemplated for use herein constitutes a departure from conventional blood culture systems. Filtration procedures have not been well accepted because of the amount of manipulations generally required to process blood. The present system, however, requires a minimum of such manipulations and offers major advantages over previous techniques involving centrifugation and filtration. For example, no lysing agents, multiple filters, dilutions, sophisticated equipment or inordinate centrifugation speeds are required or involved. Clogging of filters because of contamination with leukocytes and erythrocytes is eliminated and a minimum amount of time, e.g. less than 30 seconds, is required to filter the entire gradient. In addition, as noted earlier, the blood collecting tube, filter and media are designed to prevent contamination, the overall system being effectively sealed.

The invention is further described by reference to the accompanying drawings wherein:

BRIEF DESCRIPTION OF THE DRAWINGS

FIG. 2 is a top plan view of the apparatus;

FIG. 3 is a vertical sectional view of the apparatus on the line 3—3 of FIG. 2;

DETAILED DESCRIPTION OF THE INVENTION

Figure 8:
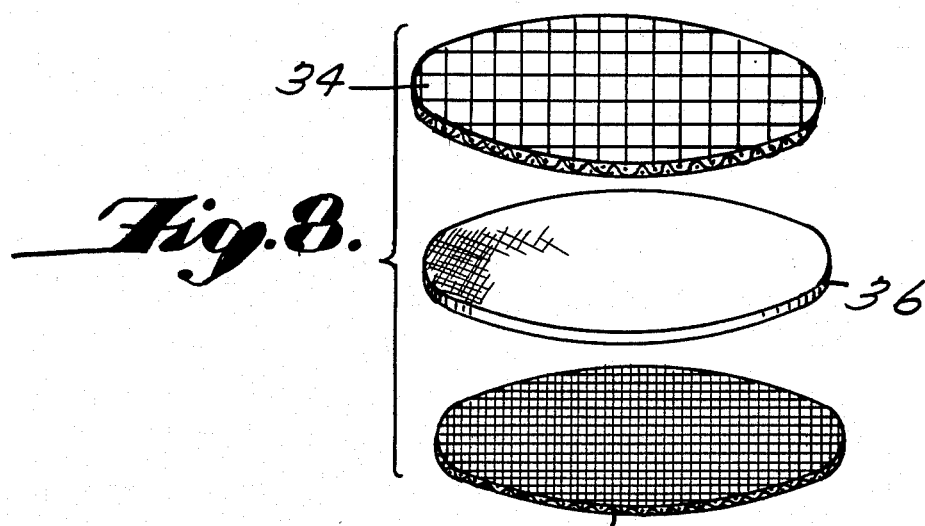
FIG. 8 is a perspective view showing separate parts of the filter unit.

Referring more specifically to the drawings, the culture system of the invention comprises a collecting and separating device (C); a filtration unit (F); and a media cup (M).

The collecting and separating device (C) is similar to the known "vacutainer" sampling system. It comprises a cylindrical glass tube (2) which is preferably composed of boro-silicate glass; a stopper (4) of butyl rubber or the like closing the top inlet end of the tube; and a vacuum coupling separation device, broadly referred to by the numeral (5), closing the other end.

The device (5) may comprise a rubber stopper (6) or the equivalent provided with a central passageway (7) which is narrowed at its inner end to support a hollow open-ended needle (8) whose inner end projects into tube (2) and is apertured as shown at (10). The other end of needle (8) empties into an enlarged zone (12) of passageway (7). A breakable membrane (14) normally extends across the passageway (7) to seal the needle (8) and interior (15) of tube (2) and avoid contamination of the tube contents. A removable seal tab (16) is also placed over the end of the tube to close passageway (7).

Tube (2) is filled with a fluid gradient or solution that can be used to collect the fluid containing the organisms to be studied. In a preferred embodiment, the fluid gradient in tube (2) is such that, for example, on centrifuging blood, erythrocytes (red blood cells) are separated by sedimentation and the remaining fluid can be used for test purposes.

Figure 1:
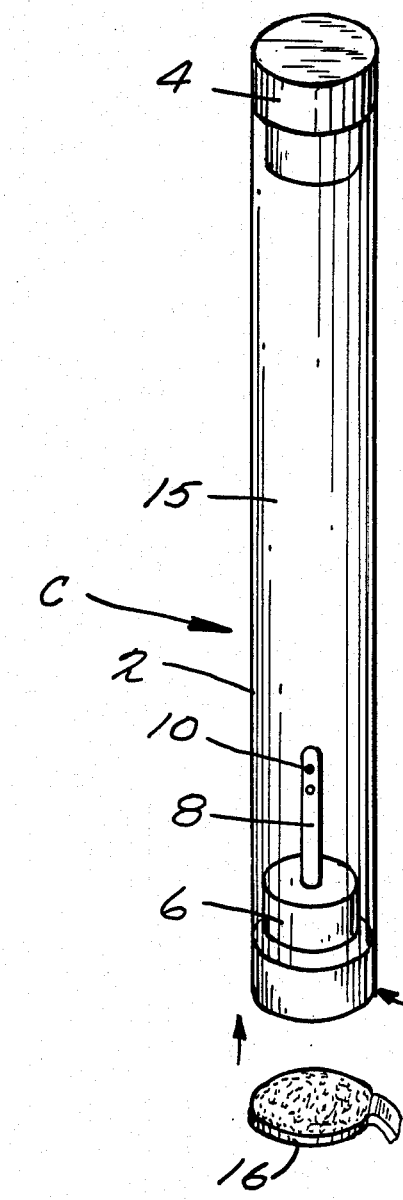
FIG. 1 is a perspective view of the collecting tube.

It will be recognized that the nature and composition of the gradient fluid in tube (2) may be widely varied and will be suitably selected depending on the fluid to be analyzed. Preferably the tube, with fluid gradient therein, is kept in the sealed, pre-sterilized condition as shown in FIG. 1 with tab (16) thereon until it is to be used. Blood or like fluid to be analyzed may be added to the tube by means of a sterile needle or the like via the top end of the tube through stopper (4) or after its removal.

A typically suitable gradient formulation and its method of preparation and use are described below:

Components

A. 90% sterile aqueous injection, e.g. Hypaque-M, 90% (brand of diatrizoate meglumine and diatrizoate sodium injection);
B. Ficoll type 400 (Sigma; cat. no. F-4375) dissolved in distilled (deionic) water (9%, Wt/vol);
C. Sodium polyanetholesulfonate (SPS) 600 mg/liter; and
D. Sodium Chloride (NaCl) 5.0 g/liter.

Formulation Preparation

For use, it is preferred to add 29 ml of saline to a bottle containing 50 ml Hypaque so as to reduce the latter's concentration from 90 to 85%. The bottle is then warmed at 37° C. to dissolve the Hypaque and kept warm for use.

Components B, C and D are then mixed together after which 800 ml of this mixture are blended with 300 ml of the warm 85% Hypague (Component A). The density of the solution is advantageously kept around 1.149.

Use

In use according to the invention, whole human blood is mixed with 10 ml of the above formulation in tube (2), the blood being added through stopper (4). The resulting mixture is then centrifuged at 2000 RPM (Sorvall Instrument GLC-4, a general laboratory centrifuge with rotor 4-1000) for 30 minutes.

As will be appreciated, the centrifuging can be carried out in conventional manner using standard non-refrigerated table top centrifuges. Centrifuging speeds in the order of 2000 to 10,000 RPM for 15 to 40 minutes usually are effective to provide the desired separation of erythrocytes although it will be appreciated that the centrifuging speed and time involved can be varied depending, for example, on the fluid being centrifuged for analysis.

Following centrifugation, the tube (2) is sealed into the assembled filtration unit (F) to filter out the organisms from the centrifuged fluid as shown in FIG. 3. More particularly, the tab (16) is removed from the tube after centrifugation is completed and the tube is then set on the top face of the filter unit (F) as shown in FIG. 3. To this end, the top surface (17) of the filter unit is provided with a circular pocket or indent (18) which is adapted to receive the tube (2) as shown. This pocket (18) is off-center with respect to the top surface of the filter unit as shown in FIG. 2. A purpose of this is to facilitate inspection of the interior of the filter unit, particularly the filter membrane, even when the tube is inserted into the unit as shown in FIG. 3. A feature of the invention is that the filter unit, and preferably also the media cup, are made from transparent molded plastic so that it is possible to easily observe the filtering of the microorganisms and their growth on the filter as herein described.

The pocket or indent (18) is provided with a centrally located hollow projection (20) which can be used to break the membrane (14) when the tube (2), after centrifugation, is placed on the filter unit. As the tube is brought downwards into indent (18), the upper end of the hollow projection, which may be provided with a razorlike cutting edge, pierces the membrane and opens up communication between the contents of tube (2) and the filter unit (F). Because of the snug fit which is provided between the tube and the indent or pocket (18), the tube contents can be effectively sealed off from contamination by the surroundings while remaining open to communication with the filter unit to effect the desired filtering operation.

In FIG. 3, the tube (2) is shown incompletely inserted into the indent or pocket (18) in order that the membrane (14) might also be illustrated. However, it will be appreciated that when the tube (2) is pushed all the way into the pocket (18), the membrane (14) is broken by projection (20) to open up the necessary communication between the interior (15) of tube (2) and the filter unit (F).

Basically, the function of filter unit (F) is to permit separation of the microorganisms by vacuum in a sealed noncontaminating environment and to support the separated organisms on the filter so that they may grow in a sealed, noncontaminable environment. As best shown in FIG. 3, the unit (F) comprises three parts, namely, the top section (21); the middle section (22) which with section (21) holds the filter (23) in place; and the bottom section (24) which connects with the vacuum source, broadly shown at (25).

The top section (21) is the unit member which is provided with the pocket (18) to receive the tube (2) in a sealed relationship as discussed above. A removable cup member (26) or the like may be provided to cover the projection (20) when the filter unit (F) is not joined to the tube (2) or otherwise not in use.

Figure 5:
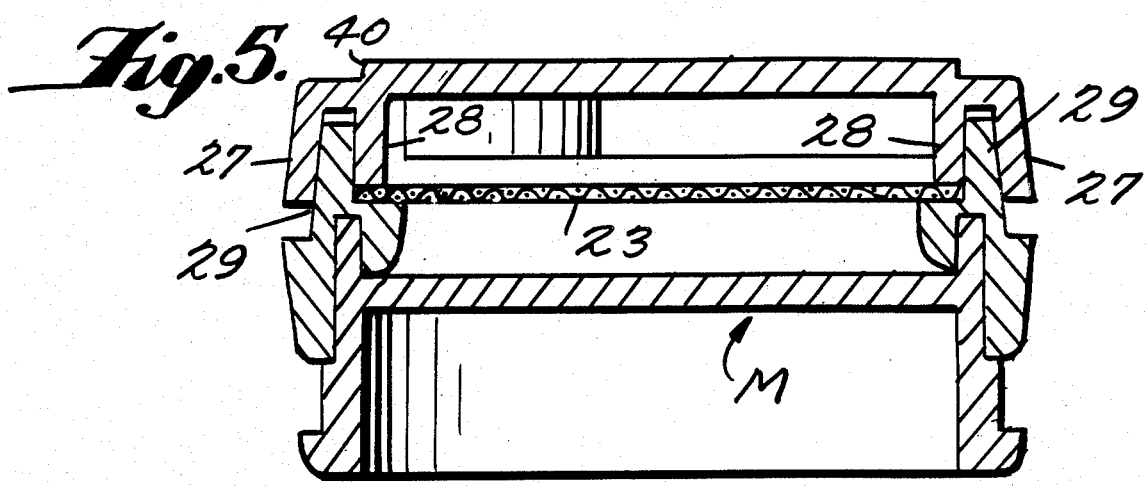
FIG. 5 is a vertical sectional view through the filter and media units.

The bottom surface of the top section (21) is provided with a pair of spaced downwardly extending ribs (27) and (28) which extend peripherally around the bottom of member (21) and are adapted to mate with an appropriately shaped upwardly extending rib (29) which extends around the upper periphery of middle section (22). This arrangement permits the filter (23) to be held firmly in place by the mating of the members (21) and (22) as shown in FIGS. 3 and 5.

The peripheries of the opposed surfaces of the middle section (22) and the bottom section (24) are also mated as shown in FIG. 3 so as to provide a compact, rigid unit (F) when the three sections are placed together.

As shown in FIG. 2, top section (21) of the filter unit (F) is essentially square in shape although other shapes, e.g. circular or oval, may be used. The middle and bottom sections may have the same shape as the top section or they may have different shapes provided the three sections can be mated together to provide a compact unit with the filter (23) in an essentially sealed condition.

Figure 7:
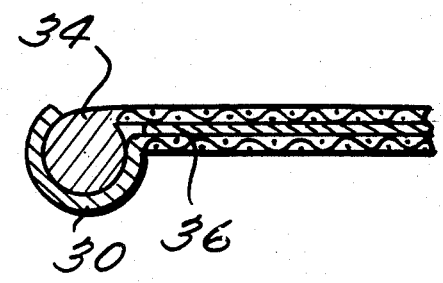
FIG. 7 is an enlarged partial section of the filter unit showing how the several parts fit together.
Figure 6:
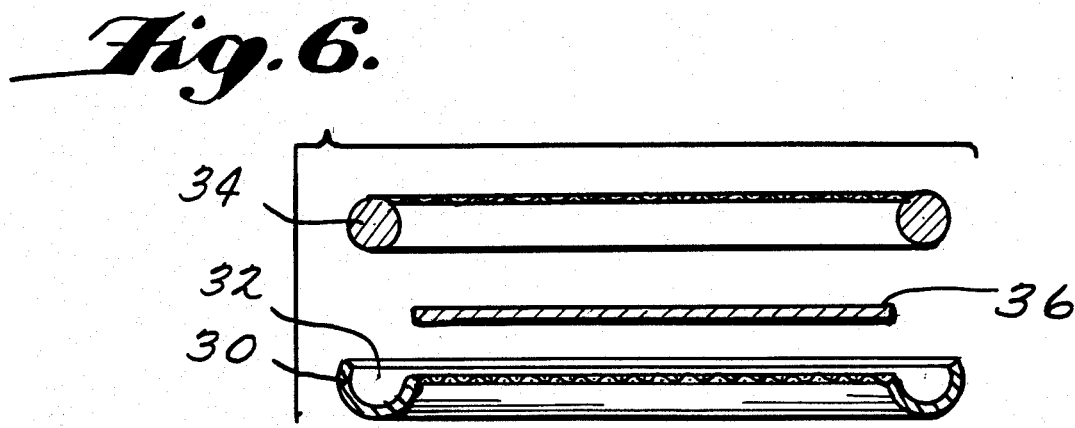
FIG. 6 is a fragmented view, partly in section, showing individual parts of the filter unit.

As shown in FIGS. 6 and 8, the filter (23) preferably comprises a support screen (30) having a circumferential trough-like periphery (32) which is adapted to receive a top grid or screen (34), the edge of the screen being shaped to fit into the support screen with a paper filter (36) firmly held therebetween as best shown in FIG. 7. Advantageously both the support screen (30) and the grid screen (34) are made from rigid plastic of sufficient strength and rigidity to hold the paper filter (36) in place and withstand the vacuum imposed during filtration and possible backflushing should the latter be desired.

The mesh sizes of the grid screen and support screen are not critical. The two screens obviously should be sufficiently open to permit the filtration to take place effectively on the paper filter while providing the desired support.

As noted, the bottom section (24) of the filtration unit (F) is provided with means (25) through which a vacuum may be drawn when the tube (2) and filtration unit have been assembled. Preferably means, for example, a removable tear or seal tab (not shown) is used to cover the vacuum connection to prevent contamination when the unit (F) is not in use, the tab being removed when the vacuum connection is to be made.

It is convenient to store the filtration units (F) in sterile condition with the three sections (21), (22) and (24) and the paper filter (23) assembled ready for use and with the top and bottom sealed by removable tabs, as indicated. A number of such units may also be stacked together generally in the manner shown in FIG. 4 although this particular FIGURE is primarily intended to illustrate how the units (F), with media cups (M) attached, can also be stacked to cultivate the media. The flat outer periphery of each filter unit lends itself to marking so that, for example, the source of a fluid being analyzed or other relevant information can be placed on the surface. Additionally, it will be appreciated that, as the filtration unit, and preferably the media cup as well, are made from transparent plastic, it is possible to easily see what is going on in any particular unit or stack of units.

When the filtration unit is to be used, the removable cup member or seal (26) is removed and a tube (2), after centrifugation and removal of the seal (16) therefrom is inserted into the pocket (18) of the filter unit as shown in FIG. 3, the tube being fully pushed down into the pocket to cause the projection (20) to break the membrane (14). The bottom seal (not shown) of the filter unit is then removed and the unit is attached to a suitable vacuum source. Vacuum is then drawn on the system and the supernatant liquid in the tube, freed of erythrocytes in the case of blood, is drawn from the tube (2) through the hollow needle (8) onto and through the filter paper (23). When filtering is complete, the bottom section (24) of the filtration unit, which acts as a general purpose receptacle for effluents passing through the filter, is replaced by a growth media cup or dish (M). See FIG. 5. Cup (M) may have generally the same outer configuration as the bottom section (24) of the filtration unit so that it mates snugly with middle section (22) as shown in FIG. 5. The elements (24 and M) are preferably cylindrical to differentiate from sections (21) and (22) of the filtration unit, which preferably have flat sides, to thus facilitate removal and insertion. Whatever the exterior shape of cup (M), however, the upper peripheral surface thereof should mate with the middle section (22) of the filter unit in the same way as the removable bottom section (24) of the filter unit. Thus, when the filtration is complete, the bottom section (24) can be removed by pulling the same downwardly away from the middle section and the media cup (M) then inserted as shown in FIG. 5.

The growth media cup (M) contains an appropriate growth medium, of the type known in the art, so as to encourage growth of bacteria collected on the filter paper (23). As shown in FIG. 5, the media cup is positioned very closely to the filter paper so that media in cup (M) will essentially contact the microorganisms and/or otherwise cause them to grow right on the filter paper.

If desired, the bottom section (24) of the filtration unit and the growth media cup (M) may be provided with serrations (38) or the like to facilitate removal.

It will be appreciated that the growth media cup should be kept in a pre-sterilized condition with the appropriate media therein for use.

Figure 4:
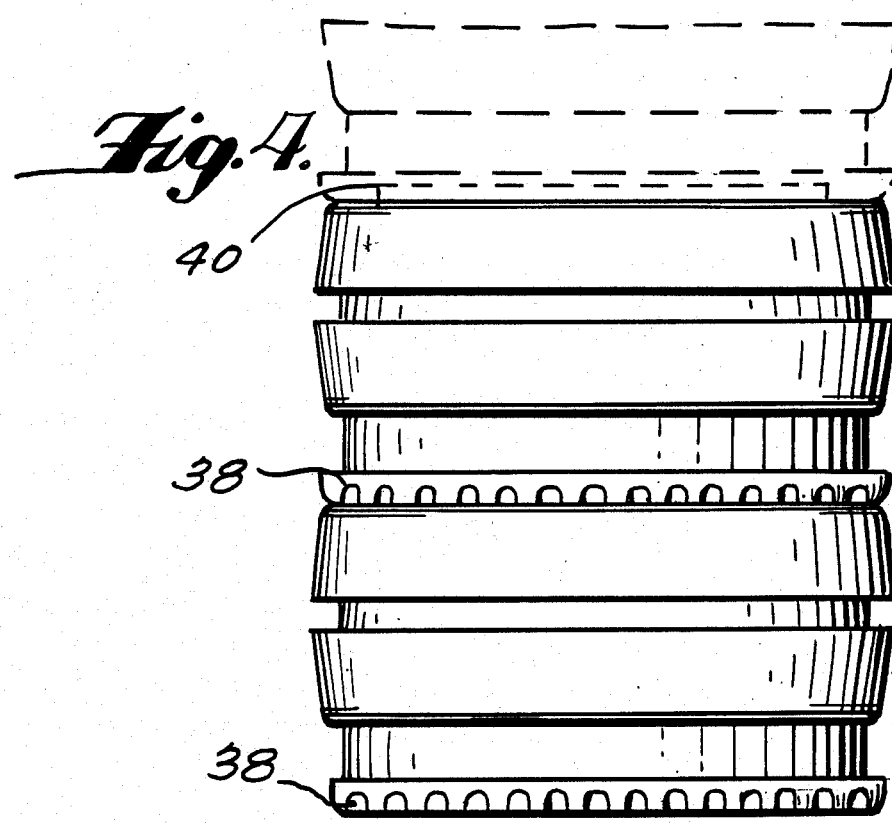
FIG. 4 is a side view of the filter and media units of the apparatus showing how these units stack together.

As noted earlier, FIG. 4 illustrates the stacking feature of the filtration units either with the bottom section (24) or with the media cup (M). The units may thus be stacked for storage or they may be stacked for cultivation of the microorganisms on the filter by means of the growth media. In this connection, it is a further feature of the invention that each of the filtration units is provided with an upper protrusion (40) which is adapted to fit into a mating recess in the bottom of an adjacent unit, thereby facilitating stacking as shown in FIG. 4.

Conventional growth media may be used for present purposes and those in the art will know which medium is preferred for selection for any particular situation in order to enhance the growth of microorganisms collected on the filter. Typical media include the following:

1. Blood Agar (Formula per liter of deionized water)

| | | |
|---|---|---|
| A. Heart peptone | 10 g | 1% |
| B. Casein/yeast peptone | 10 g | 1% |
| C. Sodium Chloride | 5 g | .5% |
| D. Agar | 15 g | 1.5% |
| E. Sterile defibrinated sheep blood | 10-50 ml | 5% |

2. Chocolate Agar (Formula per 500 ml of deionized water)

| | |
|---|---|
| A. 1. Casein/meat peptone | 15 g |
| 2. Corn starch | 1 g |
| 3. Dipotassium phosphate | 4 g |
| 4. Monopotassium phosphate | 1 g |
| 5. Sodium chloride | 5 g |
| 6. Agar | 15 |
| B. To 500 of above base, add: | |
| 1. Hemoglobin suspension (2%) | 500 ml |
| 2. Bio - X (Gibco) | 10 ml |

3. Heart Infusion Agar (Formula per liter of deionized water)

| | |
|---|---|
| A. Heart peptone | 10 g |
| B. Casein/Yeast peptone | 10 g |
| C. Sodium Chloride | 5 g |
| D. Agar | 15 g |
| E. Sheep red blood cells | 20 ml |
| F. Bio - X (Gibco) | 20 ml |

It will be appreciated that the media referred to above are mentioned only as examples of suitable media. Obviously these media can be varied in composition and concentrations to deal with specfic situations. For example, agar content can usually be varied from 1 to 15 g to accommodate for other conditions, it being essential for the filter to absorb nutrients relatively quickly.

As will also be appreciated, the media cup (M) differs from the bottom section (24) of the filtration unit in that (M) is closed at the bottom, i.e. it does not have a fitting for the application of vacuum but instead is engineered to hold the media that acts by contact or mechanical infiltration and capillary action of gelatinous material and nutrients to the organisms trapped on the filter. In this way the organisms that have been filtered out are nourished through placement of the correct medium in its appropriate cup. The only other substantive structural difference between media cup (M) and section (24) is that the bottom inner wall of section (24) is slanted inwardly towards the vacuum source (25) as shown at (42). This facilitates the removal of fluid which passes through the filter and avoids the collection of residues in section (24).

Advantageously the media cup (M) is covered with a pull tab (not shown) to assure sterility of the nutrient material until it is to be used.

In some cases where an early preliminary assessment may be desirable, it is possible to remove part of the collected microbes from the filter by back-flushing the filter with steril water and analyzing the thus removed material using conventional stain techniques.

The components of the present system are desirably kept sterile and, as will be evident, the mating sections of the filter unit and the media cup (M) have integrated into them a double wall sealing system to insure minimal contamination in use. The resulting totally closed system lends itself very readily to eliminating many of the extraneous organisms that are picked up in other systems. When used to analyze blood, the system requires centrifugation to sediment the red cells before the ingredients of the tube are withdrawn by vacuum onto the filter surface of the filter unit. Typically the filter units are approximately 50 millimeters in width and are attached to a vacuum source that allows the clinical microbiologist to process 20 or 30 specimens every 15 to 30 minutes. After filtration the bottom portion of the filtration device is removed and replaced with the specifically designed media cup as mentioned above. The function of the media, as noted, is to supply nutrients to the filter surface and allow the microorganisms that have been trapped during the filtration process to grow. The media cup and filter which thus become one unit may then be placed in an incubator, stacked with other units, if desired, according to FIG. 4, at the appropriate temperature for the specific organisms, i.e. fungi, bacteria, Rickettsiae, large virus, etc. and examined as and when desired.

The above described system can be used to detect as little as one organism per ml of whole blood and most microorganisms will be detected within a time period of 18-24 hours. While the analysis of blood is a pariculary important area of use for the invention, a much wider area of use is contemplated. Typically the invention may be used to detect microorganisms as follows:

1. Anaerobic and aerobic bacteria in whole blood;
2. Organisms in all body fluid, i.e. pleural, spinal, seminal, urine, etc.;
3. Dairy products such as milk which contain organisms;
4. Bacteria in beer and food fermentation processes;
5. Viruses in body specimens;
6. Bacteria in pediatric samples;
7. Efficacy of therapy can be checked by serial quantitation of organisms in body fluid;
8. Recovery of viruses from fecal material and blood samples;
9. E.P.A. sludge and waste water treatment samples;
10. Pharmaceutical company sterility testing, i.e. I.V. solutions, drugs, etc.;
11. Food processing testing; and
12. Potable water testing.

It has been noted when using the present system that growth initially occurs on the filter in forms of characteristic colonies. This saves a minimum of one step from conventional culture techniques and therefore an additional 12 to 24 hours up to 48 to 72 hours. Colonies on the filter may be used directly for rapid identification in any bacterial susceptibility test. Inhibitory substances may be washed away, thus allowing more effective evaluation of therapy. Differential or selective solid media or both may be used directly. Rough quantification of bacteria present is also possible on the filter. Direct recognition and possibly even identification of organisms on the filter without prior incubation may also be accomplished using monoclonal antibodies with certain indicator tags. Early recognition of multiple bacteremia is also possible.

Numerous advantages of the invention will be evident from the foregoing. These include:

1. The speed of detection of bacteremia with the present system (hereinafter called the "MOG" System) is particularly advantageous. Most microorganisms (*Haemophilus influenzae, Streptococcus spp.*, etc.) can be detected on filters within 18 to 24 hours after filtration. This is in contrast to conventional techniques where bacteria are isolated from blood culture bottles 48 to 72 hours after inoculation.

2. The system is exceptionally sensitive. For example, small numbers of microorganisms (1 to 18 organisms/ml) can be recovered on the filters. The sensitivity of the blood culture bottles, on the other hand, is unclear. For example, thioglycolate or thiol broths are not suitable for the isolation of Pseudomonas and yeast from blood. Detection of bacteria in the blood culture bottle is affected by the type of medium.

3. Antimicrobial agents and other inhibitory substances (complement, antibodies, white cells, opsonins, haptens) are removed when blood is filtered and washed. In the conventional blood culture bottle system, removal of antimicrobials requires addition of other ingredients to the blood culture bottle to inactive antimicrobials and contamination increases with each additional entry into the blood culture bottle. Complement and specific and nonspecific bactericidal antibodies are also not removed or inactivated by the blood culture media.

4. Discrete colonies form on the filters which facilitates faster identification of the infecting organisms and greatly influences therapy. This is in marked contrast to the conventional blood culture bottle where bacteria must be isolated (additional 24 hours) before identification and susceptibility to antimicrobials can be determined.

5. The present system requires about 30 minutes for centrifugation, 15-20 seconds for filtration (removal of bacterial from blood) and 5 to 10 minutes to present the media cup to the filter. Bacteria are isolated within 24 hours. In contrast, after 24 hours of incubation, blood culture bottles are inspected visually (10 to 30 minutes), subcultured (1 to 2 hours), gram stained (1 to 2 hours), examined daily (1 to 7 days), resubcultured and restained.

6. Recovery of filtered bacteria from the filter pads can be accomplished before visible colonies are observed (within 4 hours after filtration). In the conventional system, bacteria cannot be recovered. Technicians perform a blind subculture or wait 24 hours to see visual growth.

7. The present system does not clog filters. Clogging of filters made past centrifugation-filtration systems cumbersome. Bacteria are easily isolated by the system.

8. The present system also will allow quantitation of bacteria in a patient's blood. This advantage is very important. The prognosis or development of resistance to therapy can be determined. The quantitation of bacteria also helps to determine whether contaminants are present. In contrast, the blood culture bottle can perform neither of these functions.

9. Filtered bacteria can be placed on different media. Certain organisms require more nutrients. In contrast, the blood culture bottle contains only one medium and it is not satisfactory for promoting growth of all bacteria.

10. With the present system, agents to remove all antimicrobials can be incorporated in the tube and media can be inoculated with material to determine within 2 to 3 hours if bacteria are resistant to antimicrobials. Such functions cannot be performed in a blood culture bottle since bacteria are not isolated when growing in the bottle.

11. The MOG system is rapid, simple and has negligible toxicity whereas bacteria cannot be recovered from all blood culture media using the bottle system. Additionally with the latter system, the media affects the growth of bacteria. It is estimated that there are over 200 separate blood culture media available commercially today.

The following comparison between the present "MOG" system and the conventional blood bottle culture technique emphasizes the advantages of the "MOG" system:

| MOG System | Blood Bottle Culture |
| --- | --- |
| 1. Inoculate MOG System (5 min.) | 1. Inoculate blood culture medium (5 min.) |
| 2. Centrifugation of samples (30 min) | 2. Incubate blood culture bottles for 24 hours |
| 3. Filtration of samples (15-20 sec) | 3. Examine bottles visually (1 hour) |
| 4. Incubate and detect bacteria within 18 to 24 hours | 4. Remove broth from each bottle and subculture to medium (2 hours) |
| | 5. Incubate medium for 24 hours |
| | 6. Remove broth from each bottle and gram stain (1 to 2 hours) |
| | 7. Repeat steps 2 through 6 at 48 hours, 4 and 7 days after original inoculation of blood culture media |

It will be appreciated that various modifications may be made in the invention without departing from its scope as defined in the following claims wherein:

What is claimed is:

1. Apparatus for isolating and identifying microorganisms in blood or other body fluids which comprises a tubular collection vessel for body fluid which includes a fluid density gradient solution and is suitable for centrifugation to effect sedimentation of microorganisms in the body fluid, said vessel being sealed at each end thereof and including means at a first end for placing the body fluid in the vessel and means at the other end for permitting the removal of body fluid therefrom by the application of a vacuum when a seal at that end is broken, a multisection filtration unit comprising a first section provided with means for receiving said other end of the collection vessel, means in said first section for breaking the seal at said other end of the vessel when it is received by said first section, a second section nested against the bottom of the first section, a filter membrane positioned between the nested first and second sections of said filtration unit, said filter membrane being in open communication with said other end of the collection vessel when it is received by said first section, and a third section removably coupled to the bottom of said second section, means for drawing a vacuum through the bottom of said third section whereby fluid in the collection vessel is removed through said filter membrane and from the apparatus, leaving any micro-organisms in the thus drawn fluid deposited on said filter membrane, a growth media cup capable of being removably coupled to the bottom of said second section after removal of the third section such that when said media cup is coupled to said second section, growth media in the cup contacts the bottom of the filter membrane so as to permit growth of the organisms deposited on said membrane.

2. Apparatus according to claim 1 wherein the filter membrane comprises a support screen having a circumferential trough which is shaped to receive a top grid or screen, the edge of the screen being shaped to fit into the support screen with a paper filter held therebetween.

* * * * *